United States Patent [19]
Laufer et al.

[11] Patent Number: 6,106,520
[45] Date of Patent: Aug. 22, 2000

[54] ENDOCARDIAL DEVICE FOR PRODUCING REVERSIBLE DAMAGE TO HEART TISSUE

[75] Inventors: Michael D. Laufer, Menlo Park; Bruce D. Stambaugh, Anaheim; Hien V. Nguyen, Santa Ana, all of Calif.

[73] Assignee: Hearten Medical, Inc., Tustin, Calif.

[21] Appl. No.: 09/163,849

[22] Filed: Sep. 30, 1998

Related U.S. Application Data

[60] Provisional application No. 60/060,540, Sep. 30, 1997, abandoned.

[51] Int. Cl.$^7$ .................................................. A61B 18/04
[52] U.S. Cl. ................................ 606/32; 606/41; 606/49; 607/101
[58] Field of Search ................................ 606/41, 42, 45, 606/49, 50, 32; 607/98–102; 604/22

[56] References Cited

U.S. PATENT DOCUMENTS

| | | |
|---|---|---|
| 4,269,174 | 5/1981 | Adair . |
| 4,654,024 | 3/1987 | Crittenden et al. . |
| 4,658,817 | 4/1987 | Hardy . |
| 4,966,597 | 10/1990 | Cosman ..................... 606/50 |
| 5,281,218 | 1/1994 | Imran . |
| 5,314,466 | 5/1994 | Stern et al. . |
| 5,364,393 | 11/1994 | Auth et al. . |
| 5,380,316 | 1/1995 | Aita et al. . |
| 5,389,096 | 2/1995 | Aita et al. . |
| 5,397,293 | 3/1995 | Alliger et al. . |
| 5,403,311 | 4/1995 | Abele et al. ............... 606/49 |
| 5,427,118 | 6/1995 | Nita et al. . |
| 5,533,957 | 7/1996 | Aldea . |
| 5,554,152 | 9/1996 | Aita et al. . |
| 5,607,421 | 3/1997 | Jeevanandam et al. . |
| 5,620,439 | 4/1997 | Abela et al. . |
| 5,716,389 | 2/1998 | Walinsky et al. . |
| 5,722,400 | 3/1998 | Ockuly et al. . |
| 5,769,843 | 6/1998 | Abela et al. . |
| 5,779,699 | 7/1998 | Lipson . |
| 5,873,855 | 2/1999 | Eggers et al. ............. 604/114 |
| 5,893,848 | 4/1999 | Negus et al. ............... 606/41 |
| 5,899,915 | 5/1999 | Saadat ..................... 606/170 |
| 5,910,150 | 6/1999 | Saadat ..................... 606/159 |
| 5,938,632 | 8/1999 | Ellis ........................ 604/19 |
| 5,944,716 | 8/1999 | Hektner ..................... 606/45 |
| 6,030,380 | 2/2000 | Auth et al. ................. 606/41 |

OTHER PUBLICATIONS

Denton A. Cooley, et al. "Transmyocardial Laser Revascularization," Texas Heart Institute Journal, vol. 21, No. 3, (1994) pp. 220–224.

Keith A. Horvath, et al. "Transmyocardial Laser Revascularization: Operative Techniques and Clinical Results at Tow Years," The Journal of Thoracic and Cardiovascular Surgery, (May 1996) pp. 1047–1053.

Keith A. Horvath "Thoracosopic Transmyocardial Laser Revascularization," Ann. Thorac. Surg., vol. 65, (1998) pp. 1439–1441.

E. Duco Jansen et al., "Laser–Tissue Interaction During Transmyocardial Laser Revascularization," Ann. Thorac. Surg. vol. 63, (1997) pp. 640–647.

*Primary Examiner*—Michael Peffley
*Assistant Examiner*—Roy Gibson
*Attorney, Agent, or Firm*—Burns Doane Swecker & Mathis L.L.P.

[57] ABSTRACT

A minimally invasive medical or surgical device creates holes in heart tissue utilizing a needle connected to an energy source, such a radio frequency generator, a resistive heating source, or a microwave energy source. The needle is inserted into heart tissue from an interior of the heart and activated to heat the surrounding tissue in order to produce reversible tissue damage. The device consists of an energy source and regulator, electric contacts to the energy source, a catheter, and a needle at the distal end of the catheter for delivering energy to the heart tissue. The catheter is fed through the vasculature into the interior of the heart. A temperature sensor may be positioned on the needle for sensing a temperature of the heart tissue in which the needle has been inserted. Preferably, a regulator is connected to the energy source and to the temperature sensor for controlling the temperature of the heart tissue in which the needle has been inserted to about 40° C. to about 60° C. as sensed by the temperature sensor.

8 Claims, 2 Drawing Sheets

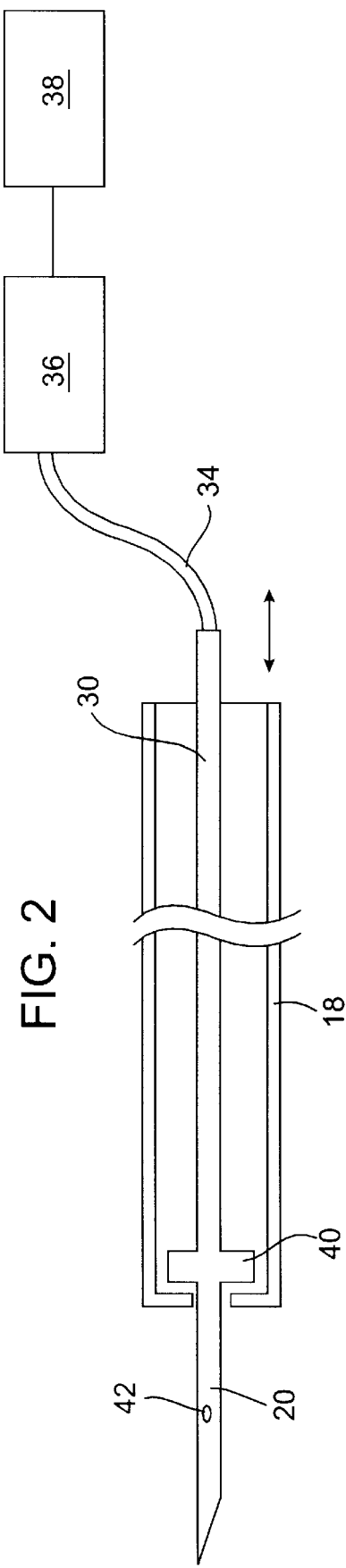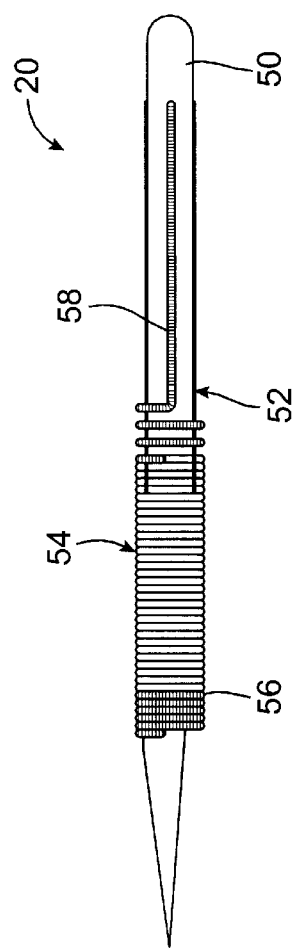

ENDOCARDIAL DEVICE FOR PRODUCING REVERSIBLE DAMAGE TO HEART TISSUE

RELATED APPLICATIONS

The present application claims the benefit of U.S. Provisional Patent Application Serial No. 60/060,540 entitled Endocardial Radio Frequency Device for Creating Holes in Heart Tissue filed Sep. 30, 1997 now abandoned.

BACKGROUND OF THE INVENTION

1. Field of the Invention

The invention relates to a medical/surgical device and method for treating the heart, and more particularly, the invention relates to a minimally invasive device and method for creating holes in heart tissue.

2. Brief Description of the Related Art

Currently there are a number of companies using lasers to create holes in heart tissue, for example, Cardiogenesis Corporation of Sunnyvale, Calif.; PLC Systems, Inc. of Franklin, Mass.; and Eclipse Surgical Technologies, Inc. of Palo Alto, Calif. Each of these companies are utilizing lasers as an energy source to vaporize heart tissue to create a plurality of holes in the heart for treating angina and heart ischemia.

Angina is severe cardiac pain most often due to ischemia of the myocardium. Ischemia is localized tissue anemia due to a partial or temporary obstruction of inflow of arterial blood. Ischemic tissue in the heart is usually found in the left ventricle due to obstruction or constriction of the coronary arteries. The procedure of forming holes in the myocardial tissue of the heart is referred to as transmyocardial revascularization ("TMR"). The purpose of TMR is to improve blood flow to under perfused myocardium. The laser created TMR holes are generally formed in the left ventricle. The holes are typically 1 mm in diameter and are placed on a 1 cm by 1 cm grid. Depending on the extent of the angina and ischemia, the laser is used to make somewhere between 10 and 50 holes. Once the holes are created, the holes are sealed off at an exterior of the heart using pressure on the epicardial surface to prevent bleeding into the pericardium.

Studies of TMR procedures on humans have had encouraging results. For example, studies have found a two class reduction in angina in some patients following TMR surgery. This two class reduction of angina greatly increases the quality of life for patients suffering from classes III and IV angina. Patients having classes III and IV angina may not be able to carry on daily activities such as walking without sever pain and may be frequently hospitalized due to heart pain. Following TMR surgery some class III and IV angina patients experience minimal or no angina for up to two years following surgery. Although these studies show that the TMR procedure improved the patients condition and quality of life, it is not yet clear how the formation of holes in the myocardium provides this marked improvement in patient condition.

Three hypophysis for the improvement which has been observed are that 1) blood flow through the TMR channels directly perfuses the myocardium, 2) damage to heart tissue from ablation and heat of the laser causes release of growth factors that result in angiogenesis, and 3) destruction of nerve pathways mask angina and prevents pain. Because the positive results of TMR surgery last up to two years, and the channels have closed by this time, it is believed that direct tissue perfusion is not the sole reason for the observed improvement.

In order to perform TMR in a minimally invasive way, the energy source may be delivered via a catheter to the left ventricle. The catheter is inserted in the arterial system of a patient and advanced retrograde through the aortic valve and into the left ventricle. The TMR holes then can be created by laser from the endocardial surface towards the epicardial surface. The laser can be controlled such that the TMR holes do not penetrate the entire wall of the left ventricle and cause bleeding into the pericardium. However, in order to perform minimally invasive TMR with a laser, a very expensive laser and fiberoptics must be utilized. The laser energy source for use in this procedure costs between about $200,000 to $700,000. This creates a high cost of performing the TMR procedure. Additionally, the laser TMR procedure vaporizes viable heart tissue which is undesirable.

Accordingly, it would be desirable to provide a cost effective, minimally invasive procedure to create transmyocardial revascularization holes in heart tissue. It is also preferable that the energy delivery system does not vaporize viable heart tissue.

SUMMARY OF THE INVENTION

The present invention relates to a minimally invasive device that creates holes in heart tissue utilizing radio frequency ("RF") energy, resistive heating, microwave energy, or the like. The device consists of an energy source and regulator, a catheter, and a needle at the distal end of the catheter for delivering energy to the heart tissue. The RF energy source, resistive heating source, or microwave source is significantly less expensive than the laser energy supply used for the known laser TMR procedure. In addition, the needle on the device does not vaporize heart tissue but instead creates a zone of reversible tissue damage caused by the heating of the tissue. Thus, the present invention provides a significant advance over the current laser TMR therapy.

In accordance with one aspect of the present invention, a medical device for treating ischemia and angina includes a catheter configured to be inserted minimally invasively from an access port through a vasculature of a patient and into an interior of a heart. A needle is positioned at a distal end of the catheter for delivering energy to heart tissue. A temperature sensor is positioned on the needle for sensing a temperature of heart tissue in which the needle has been inserted. An energy source connected to the needle and a regulator connected to the energy source and the temperature sensor controls the temperature of the heart tissue in which the needle has been inserted to about 40° C. to about 60° C. as sensed by the temperature sensor.

In accordance with a further aspect of the present invention a method of treating ischemia and angina by causing reversible damage to myocardial tissue includes the steps of inserting a needle in a minimally invasive manner through the vasculature to an interior of the heart, penetrating the myocardial tissue with the needle from the interior of the heart, heating the myocardial tissue by applying energy to the needle to create a zone of reversible tissue damage around the needle, withdrawing the needle, reinserting the needle, and heating to form a plurality of spaced apart zones of reversible tissue damage around the needle.

The present invention provides advantages of a minimally invasive TMR device which does not vaporize viable heart tissue.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 2 is a schematic cross sectional view of a TMR device according to the invention; and FIG. 3 is an enlarged side view of a resistive heating needle according to one embodiment of the invention.

DETAILED DESCRIPTION OF THE PREFERRED EMBODIMENTS

Figure 1:
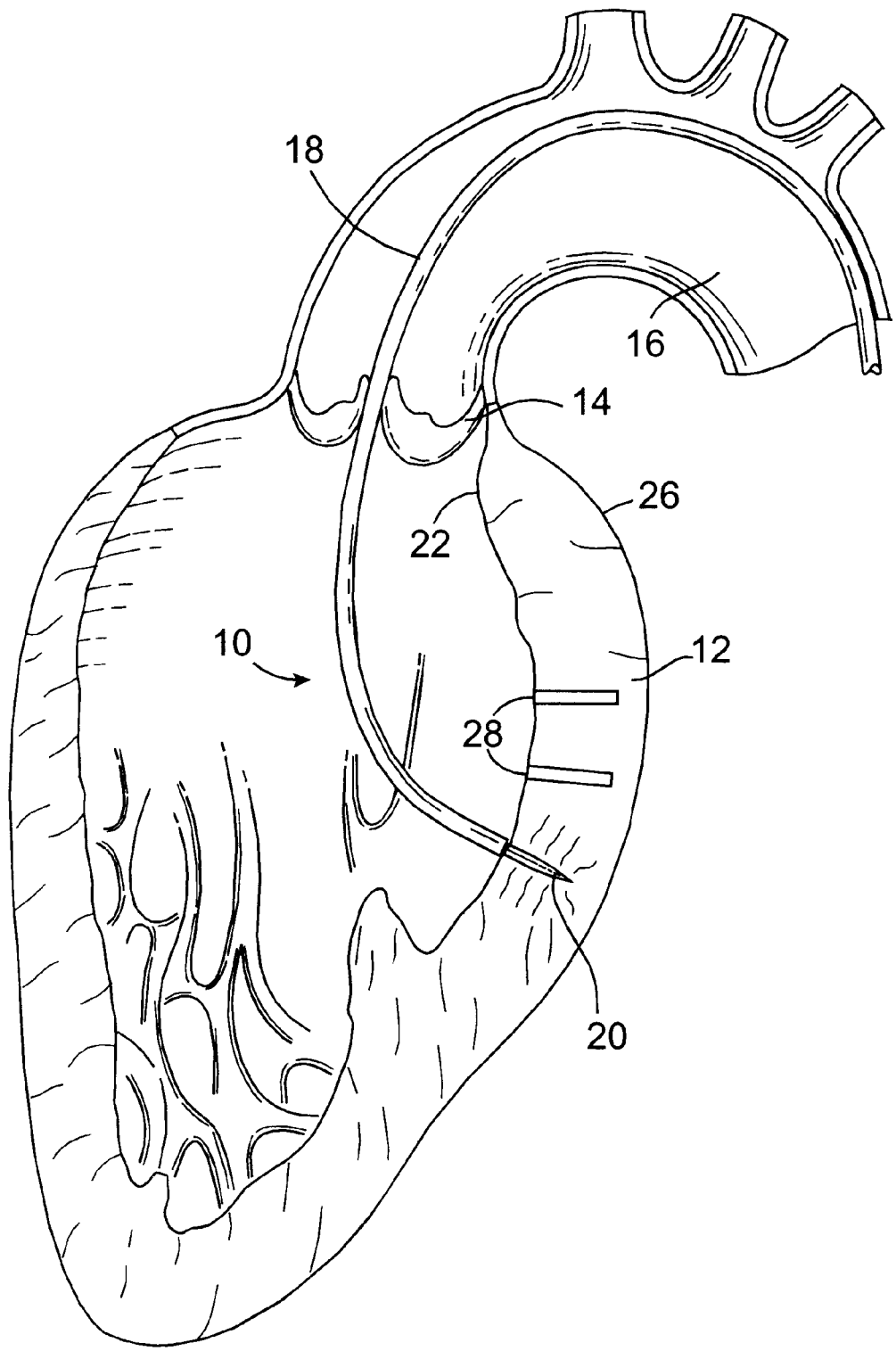
FIG. 1 is a cross sectional view of a left ventricle of a heart with a device for creating holes in the heart tissue.

The present invention provides a device and method for minimally invasive transmyocardial revascularization ("TMR") utilizing a catheter having a needle at a distal end connected to an energy source for heating heart tissue. FIG. 1 is a schematic illustration of the device 10 according to the present invention with a needle 20 inserted into left ventricular tissue of the heart from an interior of the left ventricle. In FIG. 1, the left ventricle is illustrated in cross-section with the mitral valve (the valve controlling blood flow from the left atrium to the left ventricle) not illustrated. The left ventricle wall 12 is primarily composed of heart muscle tissue. When the muscle tissue contracts, blood is expelled from the ventricle through the aortic valve 14, and into the aorta 16 for delivery of blood to the body. When the myocardium or muscle tissue is under perfused, it cannot successfully achieve the function of delivering blood to the body.

The surgical device 10 for creating holes includes a catheter 18 with a needle 20 attached at the distal end of the catheter. The needle 20 is introduced into the tissue of the left ventricle starting on the endocardial surface 22 and penetrates the myocardial tissue without penetrating the epicardial surface 26. After inserting the needle 20, the tissue surrounding the needle is heated by application of energy to the needle. As will be discussed in further detail below, the energy applied to the needle may be radio frequency ("RF") energy, inductive heating, or microwave energy.

The heating of the myocardial tissue by application of energy creates a zone of reversible tissue damage surrounding the needle 20. In accordance with the present invention, the size of the zone of reversible tissue damage is preferably maximized while the area of permanent tissue damage is minimized. This is achieved by heating the heart tissue to about 40° C. to about 60° C., preferably about 44° C. to about 50° C. for a time of between about 5 and 120 seconds. The reversible tissue damage area acts like a bruise and causes angiogenesis (creation of capillaries and arteries) and arteriogenesis (creation of small arteries). The newly created blood vessels resulting from the treatment improve tissue perfusion and relieve chronic ischemia and angina.

When energy is applied to the needle 20, the zone of reversible tissue damage created around the needle extends radially from the needle and axially from the tip of the needle. Accordingly, the zone of reversible tissue damage will preferably extend all the way through to the epicardial surface 26. Although FIG. 1 illustrates visible holes 28 formed though the myocardial tissue, in fact the holes 28 remaining when the needle 20 is removed will be very small or even imperceptible.

The diameter of the needle 20 can vary, however the preferred diameters range from about 0.1 mm to about 3 mm with 0.5 mm, 1.1 mm, 1.4 and 1.7 being presently preferred. The length of the needle can also vary to match the left ventricular wall thickness. The needle length is preferably less than a thickness of the heart tissue to prevent creating a hole all the way through the ventricle which would cause bleeding into the pericardium. Preferably, the needle 20 extends about 40–90% of the way through the heart tissue. For example, for tissue about 20 mm thick, a 8–18 mm needle, and preferably a 10 mm needle will be used. Needle lengths of about 3 mm to about 20 mm may be used. A 10 mm long needle having a diameter of 0.5 mm is presently preferred.

The needle 20 according to the RF or microwave heating embodiment may be made out of a rigid electrically conducting material such as stainless steel. The very distal end of the needle 20 is beveled to provide a sharp point for penetrating the heart tissue. The bevel, however in the RF and microwave embodiments, creates a sharp RF or microwave energy concentration that can disproportionately deliver too much energy from the needle tip. Thus, in a preferred embodiment the beveled tip is coated with a thin layer of an RF or microwave insulating material such as polyurethane.

The needle 20 can be directly attached to the distal end of the catheter 18, or can be deployably retained within the catheter and a deploying means can be provided at the proximal end of the catheter to deploy the needle. According to the RF and microwave embodiments, the RF or microwave energy being delivered by the needle may be delivered in a monopolar or a bipolar mode. Monopolar RF or microwave energy may be applied by a reference grounding pad which is attached to the skin of the patient and is connected to the energy source, the needle is also connected to the energy source to complete the circuit. A needle 20 can also be used in a bipolar mode when the needle comprises an electrode at the distal end, an area of insulating material, and an electrode at the proximal end of the needle.

The catheter 18 is preferably constructed out of standard catheter materials such as polyurethane, polyimide, and the like. Typically the catheter 18 will be extruded via well known means in the art. The catheter 18 will have at least one lumen for providing an electrical connection to the needle from the energy source. Multiple lumens may also be provided for drug delivery, visualization, and the like. The length of the catheter 18 will be such that it is long enough to place the distal end within the heart from a remote access site such as a femoral artery, typically 80 cm to 140 cm long. The diameter of the catheter 18 can vary, with smaller diameters being presently preferred. The diameters can range from about 3 French to about 10 French.

FIG. 2 illustrates one embodiment of the transmyocardial revascularization device 10 including a catheter 18 and a retractable needle 20. The needle 20 is connected to an elongated flexible rod 30 which extends through a lumen 32 of the catheter from the needle to the proximal end of the catheter. The flexible rod 30 contains electrical cables 34 for connecting the needle 20 to an energy source 36. The number of electrical cables 34 will vary depending on whether the device is a, monopolar or bipolar device and whether a thermocouple is used. The energy source 36 is preferably connected to and controlled by a controller or regulator 38.

The elongated flexible rod 30 is used to move the needle 20 from the extended position illustrated in FIG. 2 to a retracted position in which the needle is fully contained within the distal end of the catheter 18. The needle 20 is preferably provided with a stop member 40 which limits the depth of penetration of the needle into the myocardial tissue.

A standard thermocouple 42 can be provided in the lumen of the needle 20 or on an exterior of the needle 20 to give feedback on the temperature of the needle and surrounding tissue. If a thermocouple 42 is provided, then more lead wires 34 are provided in the catheter lumen to connect the thermocouple to the energy source 36 and regulator 38.

In the RF energy embodiment, the RF energy typically ranges from about 100 kHz to about 1,000 kHz, preferably about 400 kHz to about 500 kHz, and more preferably about 460 kHz. The watts of power can vary from about 0.1 watt to about 100 watts, preferably about 3 watts to 25 watts. According to one variation of the RF heating embodiment, the maximum power of the energy source 36 is set to 80 watts initially and the power is then controlled by the regulator 38 to achieve the desired temperature. Many different RF generators can be used to supply the RF energy. Presently, and RF generator manufactured by Stellartech Research Corporation of Mountain View, Calif. is preferred. The RF generator can deliver a maximum wattage of RF energy, with that maximum wattage chosen by the user of the generator. The RF generator can measure the temperature at a thermocouple inside or outside the needle to regulate the wattage to maintain a set temperature. Presently, a temperature ranging from about 40° C. to about 60° C. is used with a temperature of 44° C. to 50° C. being presently preferred. The RF energy can be delivered for a set time ranging from 1 second to 500 seconds, with 30 seconds being presently preferred.

In use, the catheter 18 is introduced into a vessel using standard catheter techniques. A commercially available introducing catheter is used to penetrate the skin of a patient and is then advanced into the vessel. Presently a Cordis Corporation, Miami, Fla. introducing catheter is used and is advanced into the femoral artery. A single lumen sheath catheter is then advanced through the introducing catheter, into the artery, retrograde through the aortic valve 14 and into the left ventricle. Once in the left ventricle, the hole creating catheter 18 having the needle 20 is then advanced through the sheath catheter and into the left ventricle. The needle 20 is then advanced into heart tissue by a health care practitioner, preferably a physician.

To ensure that the tip of the needle is in the left ventricular wall, a feedback mechanism can be used. Some appropriate feedback mechanisms can be echocardiography, electrograms taken at the very distal tip of the needle, or pressure readings at the tip of the needle. Energy is then applied to the needle, until a thermocouple in the needle reaches about 40° C. to 60° C. and then the power is controlled by the controller 38 to maintain the desired temperature of the tissue. The power is delivered for an administration period such as 30 seconds. Then the needle 20 is removed from the ventricular wall and the procedure is repeated as needed to generate the appropriate amount of holes 28 in the myocardial tissue depending on the patient's condition. When the needle 20 is removed a channel has been created in the heart to allow blood to flow in and out of the channel during the contracting of the heart muscle. Additionally, the reversible tissue damage caused by heating the tissue is the source of growth factors that initiate angiogenesis and/or arteriogenesis. Over time, the ischemic area of the heart becomes better perfused with blood and the patient with angina experiences less pain.

According to one embodiment of the present invention, the lumen of the catheter 18 can be used to deliver beneficial agents to the heart tissue during or after the TMR procedure. For example, a syringe may be attached to a lure fitting at a proximal end of the catheter 18 for delivery growth factors into the hole 28 formed by the needle 20. Examples of growth factors include vascular endothelial growth factor (VEGF), fibroblast growth factor (FGF), monocyte attracting protein (MAP), and the like.

FIG. 3 illustrates an enlarged view of a resistive heating needle 20 for producing reversible damage to heart tissue. The resistive heating device as illustrated in FIG. 3 includes a central core or wire 50 formed of a conductive material such as a 0.011 inch stainless steel wire. An insulating jacket 52 surrounds the wire 50 and provides insulation between an inner core and an outer core of the needle 20. The insulating jacket 52 may be any form of insulating tubing or coating such as polyimide tubing. Surrounding the insulating jacket 52 is a coiled resistance wire 54 which is preferably an alumel wire which provides the resistive heating of the device. The resistance wire 54 is connected to the inner core or wire 50 by a solder joint 56 at the distal tip of the needle 20. A proximal end of the coiled resistance wire 54 is electrically connected to an electrode wire 58 formed of a conductive material. The inner core wire 50 and the electrode wire 58 are connected by the electrical cables 34 (shown in FIG. 2) to the positive and negative terminals of the electric power source. A heat shrink tubing may be provided over the resistance wire 54 to completely enclose the resistive elements of the needle.

A thermocouple assembly is preferably provided over the heat shrink tubing. The provision of the thermocouple assembly at an exterior of the needle 20 allows the thermocouple to be directly in contact with the heated tissue in which the needle has been inserted to accurately sense a temperature of the tissue. The thermocouple assembly may include a thermocouple sandwiched between two insulating jackets. The thermocouple may be any known thermocouple, such as a thermocouple formed of a chrome alumel and constantan wire. Lead wires are provided to connect the thermocouple to the regulator or controller 38 for control of the heating of the tissue.

The resistive heating device according to FIG. 3 may be connected to either an AC or DC power supply. According to one embodiment of the invention, the resistive heating device is a disposable battery powered device including a battery positioned at or near the proximal end of the catheter 18 in place of the electrical cable 34.

While the invention has been described in detail with reference to the preferred embodiments thereof, it will be apparent to one skilled in the art that various changes and modifications can be made and equivalents employed, without departing from the present invention.

What is claimed is:

1. A method of treating ischemia and angina by causing reversible damage to myocardial tissue, the method comprising:

inserting a needle in a minimally invasive manner through the vasculature to an interior of the heart;

penetrating the myocardial tissue with the needle from the interior of the heart;

heating the myocardial tissue by applying energy to the needle to create a zone of reversible tissue damage around the needle; and withdrawing the needle, reinserting the needle, and heating to form a plurality of spaced apart zones of reversible tissue damage.

2. The method of treating ischemia and angina of claim 1, wherein the myocardial tissue is heated to between about 40° C. and about 60° C. with the needle to create the zone of reversible tissue damage around the needle.

3. The method of treating ischemia and angina of claim 2, wherein the tissue is heated for between about 5 seconds and about 120 seconds.

4. The method of treating ischemia and angina of claim 1, wherein the needle is inserted part way through a heart wall.

5. The method of treating ischemia and angina of claim 1, wherein the myocardial tissue is heated by applying radio frequency energy to the needle.

6. The method of treating ischemia and angina of claim 1, wherein the myocardial tissue is heated by resistance heating of the needle.

7. The method of treating ischemia and angina of claim 1, wherein myocardial tissue is heated by applying microwave energy to the needle.

8. The method of treating ischemia and angina of claim 1, wherein the myocardial tissue is heated to a temperature of between about 44° C. and about 50° C.

* * * * *